(12) United States Patent
Torno et al.

(10) Patent No.: US 8,178,648 B2
(45) Date of Patent: May 15, 2012

(54) DIAMINIUM BIS-3,5-DICARBOXYBENZENSULFONATE AND TRI-DIAMINIUM BIS-3,5-DICARBOXYBENZENSULFONATE AND METHODS FOR PRODUCING SAME

(75) Inventors: Tracy A. Torno, Batesville, AR (US); Candice Stalker, Batesville, AR (US); Maria Adriana Sousa-Ragle, Sulphur Rock, AR (US); Todd Coleman, Batesville, AR (US); Ronnie Hampton, Batesville, AR (US)

(73) Assignee: Future Fuel Chemical Company, Batesville, AR (US)

( * ) Notice: Subject to any disclaimer, the term of this patent is extended or adjusted under 35 U.S.C. 154(b) by 604 days.

(21) Appl. No.: 12/266,368

(22) Filed: Nov. 6, 2008

(65) Prior Publication Data

US 2009/0156857 A1      Jun. 18, 2009

Related U.S. Application Data

(60) Provisional application No. 61/014,674, filed on Dec. 18, 2007.

(51) Int. Cl.
*C08G 73/10* (2006.01)
*C09K 3/00* (2006.01)

(52) U.S. Cl. ... 528/313; 528/332; 528/335; 252/183.11; 562/30; 562/46

(58) Field of Classification Search .................. None
See application file for complete search history.

(56) References Cited

U.S. PATENT DOCUMENTS

| | | | |
|---|---|---|---|
| 3,475,111 A | 10/1969 | Meyer | |
| 5,889,138 A * | 3/1999 | Summers | 528/310 |
| 6,334,877 B1 | 1/2002 | Studholme | |
| 6,479,619 B1 | 11/2002 | Duan | |
| 2007/0060496 A1 | 3/2007 | Boardman | |
| 2007/0082157 A1 | 4/2007 | Heater | |

* cited by examiner

*Primary Examiner* — Yate K Cutliff
(74) *Attorney, Agent, or Firm* — Stan Baker

(57) ABSTRACT

A composition of matter comprising a diamine salt and sulfoisophthalic acid in a ratio other than one salt to one acid and a process for producing a diamine salt of sulfoisophthalic acid comprising generating a sulfoisophthalic acid and charging the sulfoisophthalic acid with diamine.

23 Claims, 4 Drawing Sheets

DIAMINIUM BIS-3,5-DICARBOXYBENZENSULFONATE AND TRI-DIAMINIUM BIS-3,5-DICARBOXYBENZENSULFONATE AND METHODS FOR PRODUCING SAME

CROSS REFERENCE TO RELATED APPLICATIONS

This application claims benefit of U.S. Provisional Application No. 61/014,674, filed Dec. 18, 2007, the entire disclosure of which is incorporated herein by reference.

BACKGROUND OF THE INVENTION

1. Field of the Invention

The present invention generally relates to the field of creating diamine salts of a free form of 5-sulfoisophthalic acid and for using those salts in treating nylon polymers.

2. Description of Related Art

Nylon is a frequently used polymer, present in carpet fibers, clothing, fishing lines, parachutes, footwear, pantyhose, toothbrush bristles, Velcro, airbags, printing plates, rope, guitar strings, racquet strings, flexible tubing, and basketball nettings, among other things. Nylon, as it is known in the art, is comprised of repeating units linked by amide bonds into monomers, which are then reacted to form long polymer chains, and is therefore also known as polyamide ("PA"). More specifically, the copolymers are formed by reacting equal parts of a diamine and a dicarboxylic acid, so that amide bonds form at both ends of each monomer. Longer polymers are achieved by creating a solid nylon salt at room temperature with a 1:1 acid-base ratio, which polymerizes at 285 degrees Celsius. Nylon can be made in several forms, including nylon 6,6; nylon 6; nylon 9; nylon 5,10; nylon 6,11; polymers with added diacids; and copolymers of these forms. Those in the art may also refer to these compounds as PA66, PA6, etc. As used herein, the term "nylon" encompasses all polyamides known to those skilled in the art or yet to be discovered.

A particularly prevalent use of nylon is as nylon fiber. While defined by the Federal Trade Commission as "a manufactured fiber in which the fiber forming substance is a long-chain synthetic polyamide in which less than 85% of the amide-linkages are attached directly (—CO—NH—) to two aliphatic groups," the term herein is used more broadly to encompass any fiber comprised of any polyamide and currently, or in the future, used in a textile.

Nylon fiber is particularly useful in carpet, and is believed to be the most commonly used fiber for carpet. This is because of its many advantages: nylon can be dyed topically or in a molten solution; is easily printed; is very durable; is abrasion-resistant; and is resistant to insects, fungi, molds, mildew, and rot. When blended with wool, it increases the carpet's durability and lowers its cost.

Nylon fibers contain many dye sites in the form of amide linkages. These sites may be filled by acidic dye molecules in order to color the polymer and ultimately the carpet. If left unfilled, the fiber can be prone to staining by acidic substances such as soft drinks, coffee, and wine.

One current way of making nylon fibers more resistant to acid dye stains is to include monomers with sulfonate moieties in the polymers. However, these sulfonate-containing compounds have higher melt viscosities that reduce the effectiveness of the melt spinning process by which nylon fibers are generally prepared, because polymerization is slower and because the polymerized nylon cannot be removed from the polymerizing machinery as easily. The sulfonate elements can also act as surfactants, which create foam during the polymerization process, and thereby disrupt the product's ultimate uniformity. Finally, the sulfonates attract water molecules, making the final product require more time to dry. In addition, polymers with sulfonate-containing monomers achieve poor stain resistance and only moderate soil resistance. Accordingly, there is a need in the industry for a method of making nylon acid-resistant which does not include sulfonate-containing monomers.

Another common way of achieving stain resistance and rapid drying is by applying a compound to the nylon fiber that acts as a topical "stain blocker" by associating with, and thereby blocking access to, the acid dye sites. Such compounds themselves also do not associate with the acid dye. One known current topical dye site blocker is sulfonated aromatic condensates. However, these compounds are only temporary and are removed from the textile or carpet during normal use, maintenance, and cleaning, even with regular detergent. These compounds are also not adequately resistant to light, nitrous oxides, and bleach, and may also alter the treated nylon fiber's colors. It is therefore desirable in the industry for a compound which has the ability to permanently impede acid dye sites, be resistant to environmental conditions such as light and detergents, and not alter the treated fiber's colors.

Another currently used molecule in treating nylon-based textiles is metal salts of sulfoisophthalic acid ("SIPA"). The acronym "SIPA" can describe a molecule with the formula of $(RO(O)C)_2ArSO_2OM$, in which each R can be the same or different, and is hydrogen or an alkyl group containing 1 to about 6 carbon atoms or hydroxyalkyl group containing 1 to 5 carbon atoms; Ar is a phenylene group; and M is hydrogen, an alkali metal, an alkaline earth metal, diamine, or combinations of two or more thereof. Of particular use in treating nylon-based textiles are the lithium and sodium SIPA salts ("LiSIPA" and "SSIPA"). Use of such metal salts in treating nylon carpet fabrics is disclosed in U.S. Pat. No. 6,334,877, to Studholme, and U.S. Pat. No. 3,475,111, to Meyer.

The presence of lithium and sodium cations, i.e., sodium or lithium SIPA salts as intermediates, in LiSIPA and SSIPA however can be problematic. They are believed to interfere with the manufacturing process, in that they contribute to a precipitate that clogs the polymerizing machinery. Sodium is believed to be particularly problematic in this regard. It is therefore desirable in the industry for the development of a metal salt of SIPA used in treating nylon that has a cation that does not precipitate in a manner detrimental to the manufacturing process.

Another problem with current metal salts of SIPA is the presence of sulfates, which, especially in the presence of lithium or sodium, is believed to generate an inorganic buildup. This buildup interferes with heat transfer, which lowers the efficiency of the manufacturing process. It also necessitates more frequent cleaning, which lowers the amount of time that can be spent manufacturing the product and requires man hours for such cleaning, which both in turn contribute to a higher cost of manufacturing the final product. It is therefore desirable in the industry for the development of a metal salt of SIPA that can be generated in a manner that minimizes the presence of sulfates.

Current production processes of these metal salts of SIPA generate the salt of SIPA. However, these current processes do not isolate the salt formed between the diamine and acid, but instead isolate and use SSIPA. Given the lingering presence of a sodium cation, these processes do not solve the aforementioned problem of sodium-based precipitates.

Another current process charges a reaction unit with deionized water, then SSIPA, in order to make a solution. The solution is then charged with 80% hexamethylene diamine ("HMDA") in 20% water, after which the HMDA replaces the sodium as the cation. This process does achieve the stated goal of producing a SIPA salt without sodium as its cation. However, this process generates a good deal of free sodium ions when the HMDA replaces sodium as the salt's cation. This results in a large amount of sodium present in the solution which, as explained above, can adversely affect the polymerization process by precipitating. It is therefore desirable for the final HMDA salt to be generated without the sodium salt of SIPA as an intermediate. It is also desirable, for the sake of efficiency and lowering the amount of raw materials used, to eliminate superfluous steps in processes for manufacturing HMDA-SIPA.

U.S. Pat. No. 3,475,111 to Meyer mentions preparing the 1:1 HMDA salt of SSIPA for use in occupying nylon acid dye sites. However, Meyer does not disclose a salt with one or three HMDA molecule(s) to two SIPA molecules, nor does it disclose any method or process of preparation of any form of a HMDA salt. It is believed that the 1:1 salt is more difficult to isolate than the 1:2 salt, as it is less prone to crystallization and is much more soluble. The 1:2 salt is therefore believed be more desirable, for those in the industry as it is more accessible. Therefore, there remains a need in the industry for the ability to generate a readily isolated HMDA salt of a SIPA without generating precipitates that adversely affect the manufacturing process.

SUMMARY OF THE INVENTION

The following is a summary of the invention in order to provide a basic understanding of some of the aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems known to those of skill in the art, described herein, among other things, is a composition of matter comprising a diamine salt and SIPA in a ratio of other than one salt to one acid. In an embodiment, said diamine is in a one to two ratio with said sulfoisophthalic acid. In an embodiment, said diamine is in a three to two ratio with said sulfoisophthalic acid.

In an embodiment, said composition comprises a mixed salt further comprising three diamine groups, wherein each of said diamine groups is different. In an alternate or further embodiment, said composition comprises a mixed salt further comprising three diamine groups, wherein two of said diamine groups is different from the third of said diamine groups. In an alternate or further embodiment, said composition comprises three diamine groups, wherein all of said diamine groups are the same.

Also disclosed herein is a process for producing a diamine salt of SIPA comprising: generating a SIPA; and charging said SIPA with a diamine, wherein said SIPA is a free acid.

In a further embodiment, said step of generating comprises adding isophthalic acid to oleum 30% to create a mixture at a first temperature range of about 60° C. to about 80° C.; heating said mixture to a temperature between about 190° C. to about 210° C.; holding said mixture at a temperature between about 190° C. to about 210° C.; cooling said mixture to about less than 170° C.; adding said mixture to a quantity of water to create an aqueous solution, while keeping the temperature below about 125° C.; cooling the mixture to temperature about 0° C. to about 125° C.; charging a diamine while keeping temperature between about 0° C. to about 125° C.; holding said mixture at a temperature between about 0° C. to about 125° C.; cooling said mixture to a temperature between about 0° C. to about 50° C.; holding said mixture to a temperature between about 0° C. to about 50° C.; filtering said solution to isolate a solid; washing said solid; and drying said solid, wherein said solid is solid diaminium bis-3,5-dicarboxybezensulfonate (DA-BisSIPA).

In an embodiment, in said step of charging, said diamine is in a one to two ratio with said SIPA. In an embodiment, in said step of charging, said diamine is in a three to two ratio with said SIPA. In an embodiment, said salt is tri-diaminium bis-3,5-dicarboxybenzensulfonate (TriDa-BisSIPA).

In a further embodiment, the process of generating further comprises: adding the solid DA-BisSIPA to a solvent at a temperature between about 50° C. to about 125° C.; adding a diamine while holding the temperature between about 50° C. to about 125° C.; holding the mixture at a temperature range of about 50° C. to about 125° C.; cooling said mixture to a temperature between about 0° C. to about 50° C.; holding said mixture at a temperature between about 0° C. to about 50° C.; filtering said mixture to isolate a solid and drying said solid; washing said solid; and drying said solid, wherein said solid is a TriDA-BisSIPA.

DESCRIPTION OF PREFERRED EMBODIMENT(S)

The following description illustrates by way of example and not by way of limitation.

Figure 1:
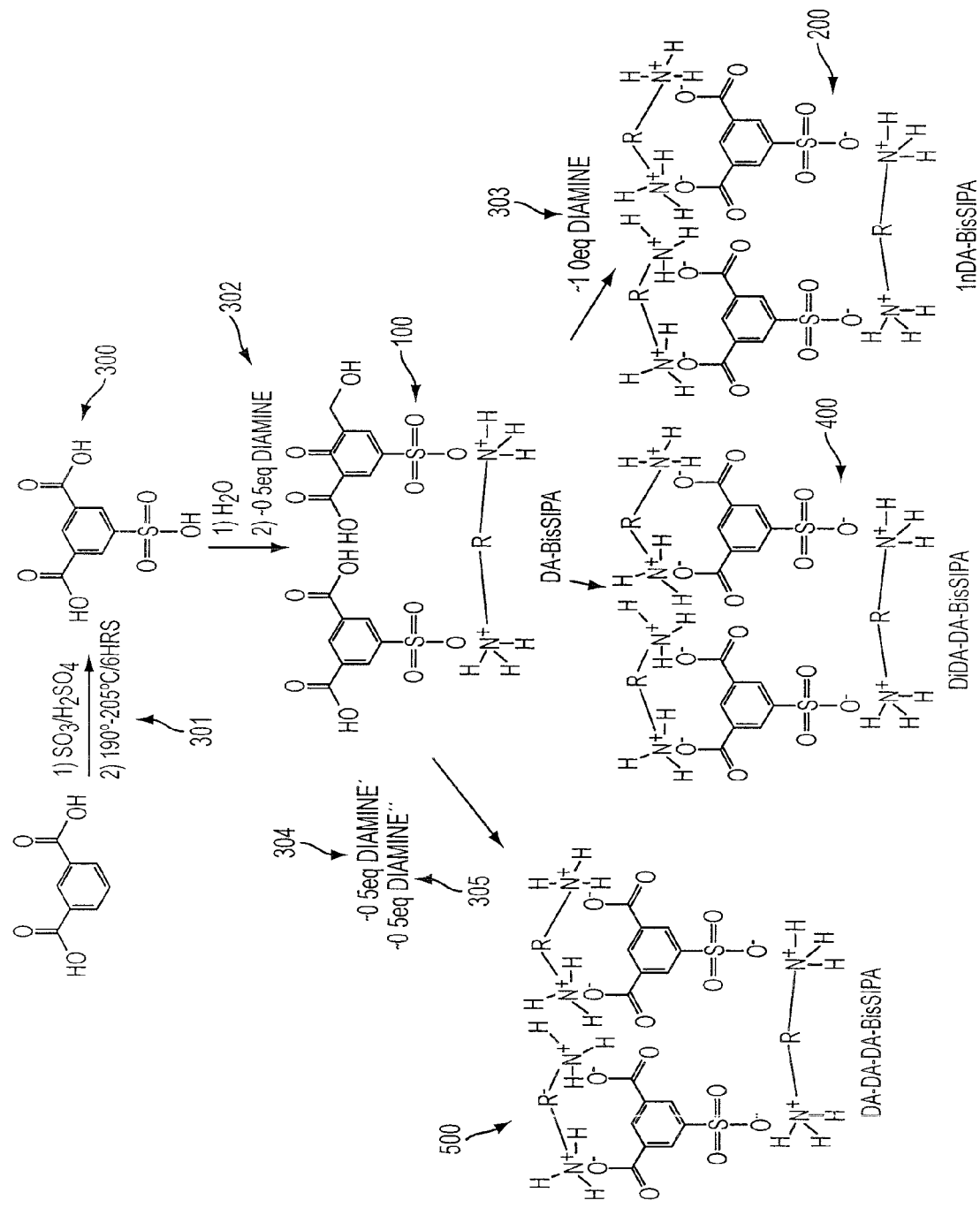
FIG. 1 provides flowcharts of an embodiment of a process for making DA-BisSIPA and TriDA-BisSIPA, among other compounds, and provides molecular diagrams of those molecules.

Generally disclosed herein are diaminium ("DA") salts of SIPA. These salts include DA-BisSIPA (100, 700), TriDA-BisSIPA (200, 710), and mixed salts (400, 500, 715, 720). These molecules and the chemical reactions of which they are a product are shown in FIGS. 1 and 4. Also disclosed herein is a process by which such salts may be generated, as set forth in FIGS. 2 and 3.

It is contemplated that the DA-SIPA molecules formed by the processes disclosed herein may also take the form of any of the following compounds or their equivalent: 1,6-hexanediamine bis-3,5-dicarboxybenzensulfonate; 1,4-butanediamine bis-3,5-dicarboxybenzensulfonate; 1,10-decanediamine bis-3,5-dicarboxybenzensulfonate; mixture of the 2,2,4- and 2,4,4-trimethyl 1,6-hexanediamine bis-3,5-dicarboxybenzensulfonate; 4,4'-methylenebis (cyclohexylamine)bis-3,5-dicarboxybenzensulfonate, N,N'dimethylethylenediamine bis-3,5-dicarboxybenzesulfonate, and N,N,N'N'-tetramethylethylenediamine bis-3,5-dicarboxybenzensulfonate. Generally, any DA salt currently, or in the future, known to those skilled in the art is contemplated; while preferred embodiments have straight, branched, or cyclic aliphatic chains, aromatic chains are also contemplated, however, such chains are not limiting or exclusive.

Further, any SIPA currently, or in the future, known to those skilled in the art is contemplated.

Also contemplated are mixed salts, created by a process where the DA-BisSIPA is treated with one or two different diamines to make a DiDA-DA'-BisSIPA or DA"-DA'-DA-BisSIPA.

FIG. 1 and FIG. 4 show a series of reactions for preparing the DA-SIPA salts. This reaction may be carried out by the following process embodiment. In step (301), isophthalic acid may be added to oleum 30% while maintaining an elevated temperature. The mixture may be heated and held. At the end of the hold, the mixture may be cooled. When the temperature of the mixture is less a critical value it may be transferred into a flask or other appropriate reaction vessel known to those skilled in the art containing pre-cooled water while keeping the aqueous solution temperature below a fixed value. The solution, containing SIPA in its free form (300), may then be cooled and the free SIPA (300) may then be used in any manner known to those skilled in the art.

Once the free acid (300) is generated, it may then be neutralized with a diamine. Different embodiments may utilize primary, secondary or tertiary amines. In FIG. 1, an embodiment of this reaction is shown as element (302) which is composed of primary amines. In FIG. 4, an embodiment of this reaction is shown as element (705) which is comprised of non-primary amines. In a further embodiment of step (302) and (705), a diamine or a diamine in a solvent may be added to the free SIPA (300) in solution while maintaining the temperature. In an alternative embodiment, the diamine may be added to the free SIPA (300) in solution at higher temperatures and the temperature lowered after the addition is complete. In an embodiment, diamine in a solution may be added dropwise. This diamine acts in place of currently used sodium or lithium ions to generate the salt of the SIPA. However, any ratio of DA to free acid that results in a compound that readily crystallizes and can be isolated may be used. In an embodiment, the molar ratio of DA to free acid will be one to two. In an alternative or contemporaneous embodiment, the molar ratio of DA to free acid will be three to two.

The material may be then stirred or otherwise continuously mixed while maintaining the lower temperature. The solid may be isolated by filtration or any other suitable means. It may also be washed in any means known to those skilled in the art, including but not limited to by water, acetone, hexane, and/or methanol, and chilled quantities of those solvents. It may then be dried by any means known in the art. In an embodiment, this reaction generates DA-BisSIPA (100) in FIG. 1 or (700) in FIG. 4, although it is contemplated that any DA-BisSIPA, TriDA-BisSIPA, any of the salts discussed above, mixed salts, or any other equivalent salt may be generated.

TriDA-BisSIPA salts (200) or mixed salts (400, 500) in FIG. 1 or tri-DA SIPA salts (710), or mixed salts (715, 720) in FIG. 4, may be prepared by dissolving DA-BisSIPA (100) or (700) in FIG. 4, into a suitable solvent known in the art and treating it with a diamine or any suitable solution of diamine in a solvent. FIG. 1 shows an embodiment of this step as element (303). FIG. 4 shows an embodiment of this step as element (708). The diamine may be the same as that diamine used in step (302) in FIG. 1 or (705) in FIG. 4, as is shown in step (303) in FIG. 1 or (708) in FIG. 4, or may be an alternative diamine. The resultant molecule may be described as TriDA-BisSIPA.

Alternatively, the diamine may be different from the diamine used in step (302); in FIG. 1 or (705) in FIG. 4, these different diamines are demarcated "diamine'" and "diamine''" in steps (304) and (305) in FIG. 1 or (706) and (707) in FIG. 4, respectively. For example, the diamine treatment may comprise a solution of 0.5 of an equivalent of each of diamine and diamine', as in steps (304) and (305) in FIG. 1 or (706) and (707) in FIG. 4, resulting in a mixed salt such as that shown as element (400) in FIG. 1 or (715) in FIG. 4. Element (400) in FIG. 1 or (715) in FIG. 4 may be described as di-DA'DA-BisSIPA or by any other accurate chemical nomenclature known in the art. Similarly, the diamine treatment may comprise a solution of 0.5 of an equivalent of each of diamine' and diamine'', as in steps (304) and (305) in FIG. 1 or (706) and (707) in FIG. 4, resulting in a mixed salt such as that shown as element (500) in FIG. 1 or (720) in FIG. 4. Element (500) in FIG. 1 or (720) in FIG. 4 may be described as DA"-DA'-DA Bis-SIPA or by any other accurate chemical nomenclature known in the art. The selection among diamine, diamine', and diamine" may be guided by, among other considerations, properties that the diamine group(s) may lend to the ultimate TriDA salt, such as solubility or other properties.

The final TriDA-BisSIPA product (200, 400, 500) in FIG. 1 or (710, 715, 720) in FIG. 4 can then be isolated. In an embodiment, the final TriDA product is isolated by filtration and washed several times with any one or a combination of different solvents, but by no means is this exclusive. This disclosure contemplates any form of isolation known to those skilled in the art. The salt can then be dried or dissolved in any suitable solvent known in the art to make a solution.

In a further embodiment, the solid is washed several times with different solvents known in the art, including but not limited to acetone and methanol.

In an embodiment, the final product can be left in its dry form; in an alternative embodiment, it may be dissolved in a suitable solvent known in the art to make a solution. For distribution, in an embodiment, the final product may be packaged in drums or bulk bags, although other forms of packaging used in the art are contemplated.

These processes of creating DA-BisSIPA (100) and other molecules (200, 400, 500) in FIG. 1 or DA-BisSIPA (700) and other molecules (710, 715, 720) in FIG. 4 accomplish several goals. First, they do not require a step in which the sodium salt, or any other metallo salt, of SIPA is generated; the first generated salt has DA as its cation. This attribute, in combination with the absence of sodium or lithium as a cation in any intermediate, eliminates undesirable levels of those ions from forming, which in turn eliminates formation of a precipitate that may interfere with the manufacturing process. In an embodiment, residual sulfuric acid, measured as sodium, may be as low as 0.02%. This eliminated step also improves the efficiency of the process of generating DA-BisSIPA and similar compounds. Such efficiency is desirable because it uses less raw materials, introduces fewer opportunities for human error, and may proceed more quickly and require fewer manhours. In addition, it is believed the embodiments wherein the DA and free acid are in a 1:2 or 3:2 ratio are relatively easy to isolate.

The resultant DA-BisSIPA (100, 700) and other molecules generated by the processes disclosed herein are believed to act as an effective acid dye site filler for nylon polymers, suitable as a stain blocker, a dye blocker, or any other use known currently or in the future in the art. Other potential products of the reaction shown in FIG. 1 and FIG. 4, including those that may be described as TriDA-BisSIPA (200, 710) and mixed salts (400, 500, 715, 720), are also contemplated to be useful in polyesters products in cases where alkali or alkaline earth metal contamination is detrimental. These molecules may have other useful properties depending on the diamine used in steps (303, 304, 305, 706, 707, 708). TriDA-BisSIPA (200) and mixed salts (400, 500) may also be used as a monomer in actually generating a dye site resistant polymer. TriDA-BisSIPA (200) and (710) may also have other uses, as they are believed to be highly soluble in water, and may be subject to a good deal of steric tension and resultant instability.

In an embodiment, the final polymer may be polymerized by any means known or discovered in the art. In a further embodiment, polymerization may be with nylon salt. In a further embodiment, the amount of DA-BisSIPA or TriDA-BisSIPA may be adjusted in order to result in a desirable final amount of SIPA in polymer. Polymerization is a particularly usable embodiment where the free sulfates have been removed, for example by barium hydroxide and filtration.

Figure 2:
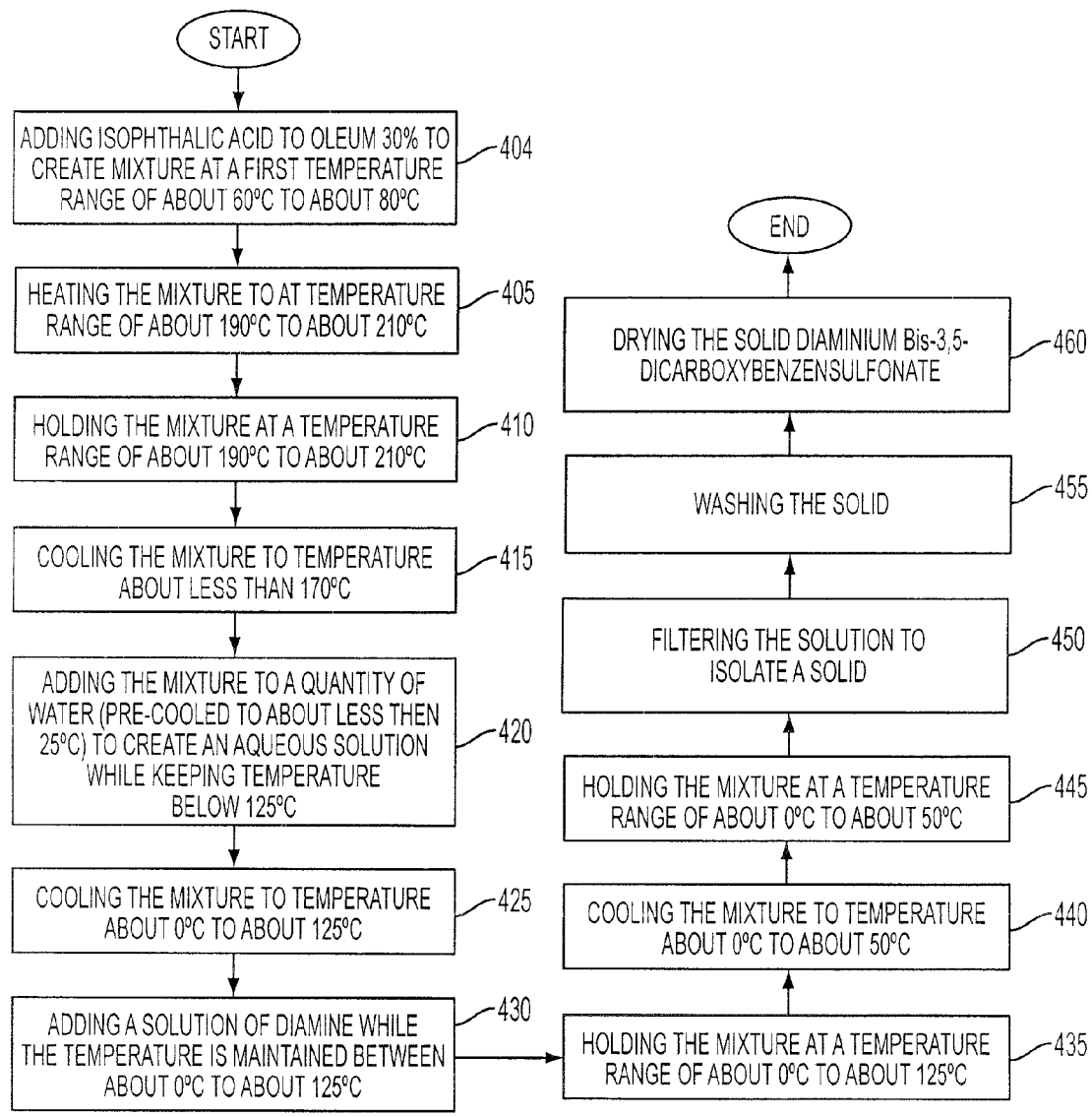
FIG. 2 provides a flowchart of an embodiment of a method for producing a DA-BisSIPA salt.

An embodiment of a procedure for the production of a DA-BisSIPA salt is shown in the flowchart of FIG. 2. In this embodiment, in a first step, isophthalic acid is added to oleum 30% to create a mixture at a first temperature range of about 60° to about 80° C. (404). In a second step, the mixture is heated to a temperature between about 190° C. to about 210° C. (405). In a third step, the mixture is held at a temperature between about 190° C. to about 210° C. (410) for a predetermined time to complete the reaction. In a fourth step, the mixture is cooled to about less than 170° C. (415). In a fifth step, the mixture is added to quantity of water (pre-cooled to less than 25° C.) while keeping the temperature of the mixture below 125° C. (420). In the sixth step, the mixture is cooled to a temperature between about 0° C. to about 125° C. (425). In a seventh step, a solution of diamine is added to the mixture while the temperature is maintained between about 0° C. to about 125° C. (430). In an eighth step, the temperature of the aqueous solution is maintained between about 0° C. and about 125° C. (435). In a ninth step, the mixture is cooled to a temperature between about 0° C. to about 50° C. (440). In a tenth step, the temperature of the aqueous solution is maintained between about 0° C. and about 50° C. (445). In an eleventh step, the solution is filtered, by a means known to those skilled in the art, to isolate the solid (450). Next, in a twelfth step, the solid is washed, by any means known to one skilled in the art (455). After washing, in the final step, the solid DA-BisSIPA is dried by any means known to one skilled in the art (460).

Figure 3:
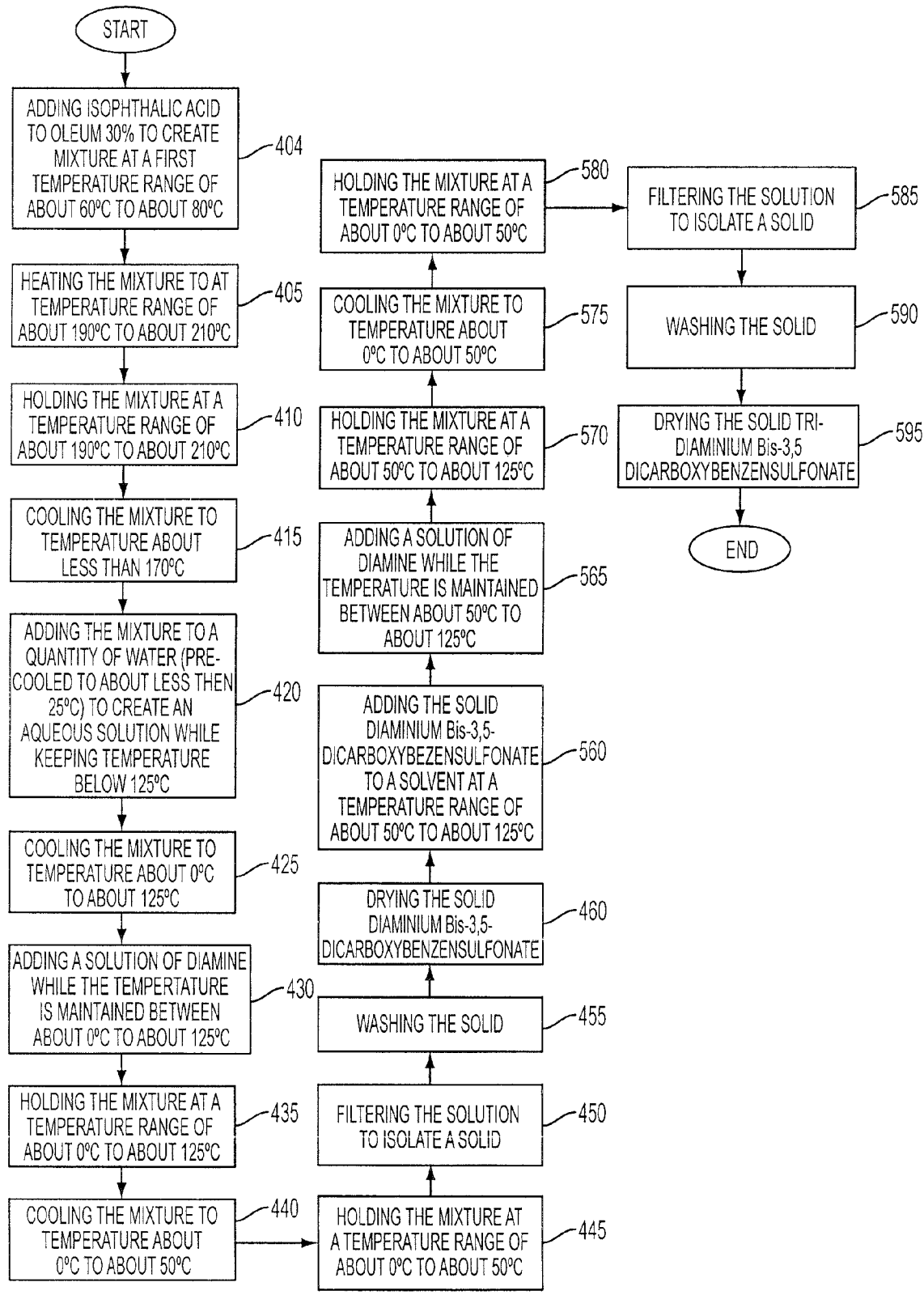
FIG. 3 provides a flowchart of another embodiment of a method for producing a TriDA-BisSIPA salt.
Figure 4:
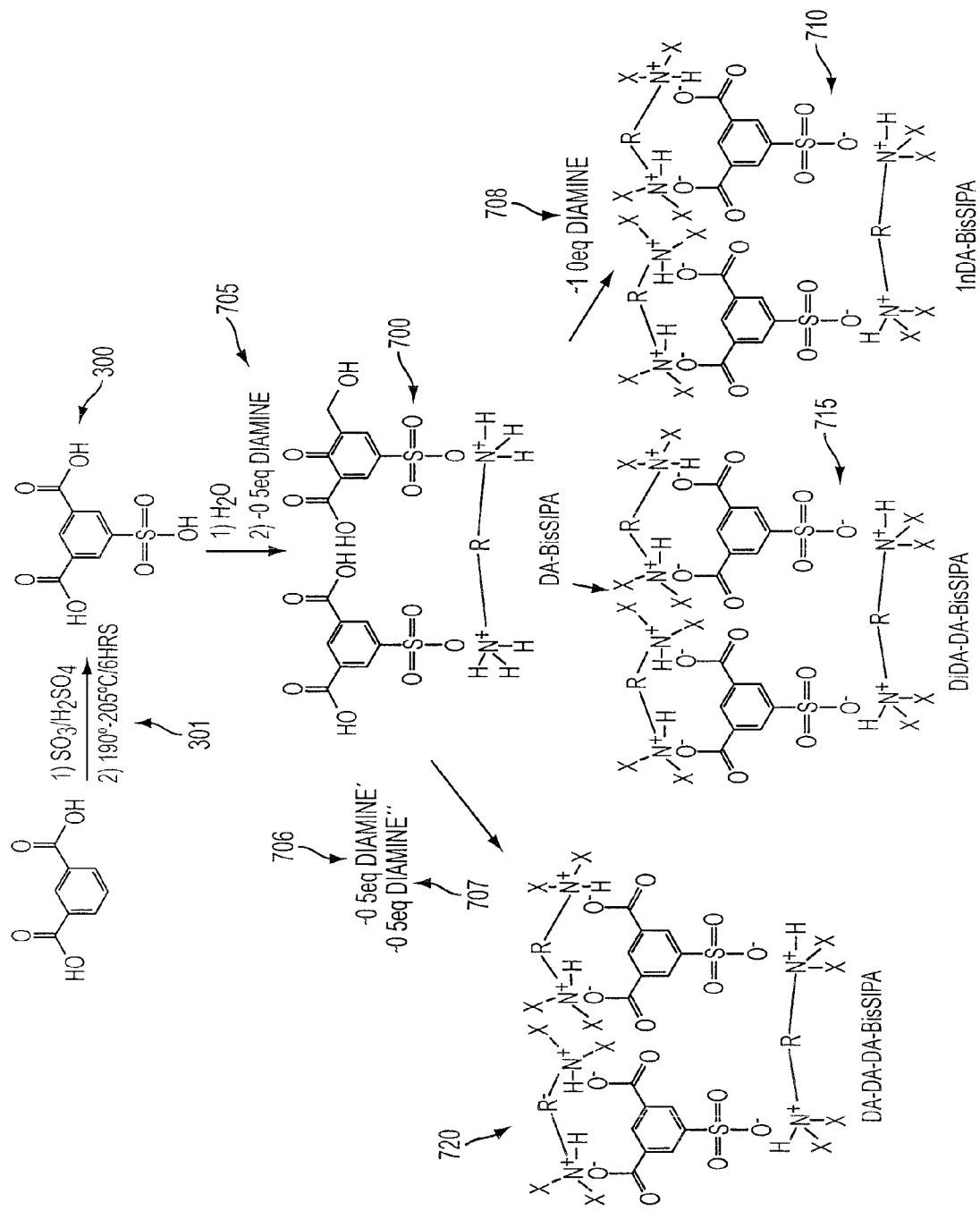
FIG. 4 provides another flowchart of an embodiment of a process for making DA-BisSIPA and TriDA-BisSIPA, among other compounds, and provides molecular diagrams of those molecules.

An embodiment of a procedure for the production of a TriDA-BisSIPA salt is shown in the flowchart of FIG. 3. In this embodiment, the initial steps are similar to those discussed above in conjunction with creating the initial diaminium bis-3,5-dicarboxybenzensulfonate. From the DA-BisSIPA solid, in a thirteenth step, the solid DA-BisSIPA is added to a solvent to make a mixture and placed in a temperature range of about 50° C. to about 125° C. (560). In a fourteenth step, a solution of diamine is added to the mixture while the temperature is maintained between about 50° C. to about 125° C. (565). In a fifteenth step, the temperature of the aqueous solution is maintained between about 50° C. and about 125° C. (570). In a sixteenth step, the mixture is cooled to a temperature between about 0° C. to about 50° C. (575). In a seventeenth step, the temperature of the aqueous solution is maintained between about 0° C. and about 50° C. (580). In an eighteenth step, the solution is filtered, by any means known to those skilled in the art, to isolate the solid (585). Next, in a nineteenth step, the solid is washed, by any means known to one skilled in the art (590). After washing, in a final step, the solid TriDA-BisSIPA is dried by any means known to those skilled in the art (595).

The resultant DA-BisSIPA salt and other molecules generated by the processes disclosed herein are expected to function in man-made fibers and polymers in the following ways: in PET Fiber, it has cationic-dyeable sites, low pill, and anti-static properties (apparel, furnishings); in Nylon Fiber, it has cationic-dyeble SITUS/stain resistance, low pill, lubricity for improved spinning, and lower viscosity (carpet, furnishings); in PET Polymer, it has water dispersibility functions (textile sizing, personal care, coatings, adhesives, detergents, paper); and in sulfonated polyester toners, it functions as a negative charge (copier/printer cartridges). These functions are not limiting, as this disclosure contemplates any plausible SIPA functions currently, or in the future, known to those skilled in the art.

The following examples are given to further illustrate, but not limit the process of this invention.

Example 1

Into a 1-liter Reaction Flask charge 105.6 g of 30% Oleum. Next charge 54.8 g of Isophthalic acid into the Reaction Flask while maintaining temperature between 60° and 80° C. Heat the contents in the Reaction Flask to 190-210° C. and hold for six hours. Prepare a 2-liter Drowning Flask by charging 319.6 g of Water into the flask. Cool the contents in the Drowning Flask to 0-5° C. Cool the contents in the Reaction Flask to 150-170° C. Transfer the contents of the Reaction Flask into the Drowning Flask maintaining the temperature in the Drowning Flask below 120° C. Cool the contents in the Drowning Flask to less than 100° C. Charge drop wise 23.8 g of an 80% 1,6-Hexamethyldiamine solution in water to the Drowning Flask while keeping temperature below 100° C. Hold the contents of the Drowning Flask for 15 minutes while keeping temperature below 100° C. Cool the contents of the Drowning Flask to less than 50° C. and hold for 15 minutes. Collect the solid product on a filter. Wash the solid on the filter with Water and Methanol. Dry the product in an oven for at least a day. 87.8 g of 1,6-hexanediamine bis-3,5-dicarboxybenzensulfonate was obtained with an assay of 99.1% and a % Yield of 87.1%.

Example 2

Into a 1-liter Reaction Flask charge 105.6 g of 30% Oleum. Next charge 54.8 g of Isophthalic acid into the Reaction Flask while maintaining temperature between 60° and 80° C. Heat the contents in the Reaction Flask to 190-210° C. and hold for six hours Prepare a 2-liter Drowning Flask by charging 319.6 g of Water into the flask. Cool the contents in the Drowning Flask to 0-5° C. Cool the contents in the Reaction Flask to 150-170° C. Transfer the contents of the Reaction Flask into the Drowning Flask maintaining the temperature in the Drowning Flask below 120° C. Cool the contents in the Drowning Flask to less than 85° C. Charge 24.1 g of N,N,N', N'-Tetramethylethylenediamine to the Drowning Flask while keeping temperature below 100° C. Hold the contents of the Drowning Flask for 15 minutes while keeping temperature below 85° C. Cool the contents of the Drowning Flask to less than 35° C. and hold for 15 minutes. Collect the solid product on a filter. Wash the solid on the filter with Water and Methanol. Dry the product in an oven for at least a day. 69.7 g of N,N,N',N'-Tetramethylethylenediamine bis-3,5-dicarboxybenzensulfonate was obtained with an assay of 99.1% and a % Yield of 69.1%.

Example 3

Into a 1-liter Reaction Flask charge 30 g of Hexane and 5.1 g 1,6-hexanediamine bis-3,5-dicarboxybenzensulfonate.

Charge drop wise 2.4 g of an 80% 1,6-Hexamethyldiamine solution in water to the Reaction Flask while keeping temperature below 60° C. Hold the contents of the Reaction Flask for over 15 hours while keeping temperature below 60° C. Charge 30 g of Hexane to the Reaction Flask. Heated the contents of the Reaction Flask to reflux and held for 60 minutes. Cool the contents of the Reaction Flask to less than 50° C. and hold for 15 minutes. Collect the solid product on a filter. Wash the solid on the filter with Hexane and Acetone. Dry the product in an oven for at least a day. 6.6 g of Tri-1, 6-hexanediamine bis-3,5-dicarboxybenzensulfonate was obtained with an assay of 98.1% and a % Yield of 94.1%.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention. Accordingly, it is intended that all reasonably foreseeable additions, modifications, deletions and alterations be included within the scope of the invention as defined in the following claims.

The invention claimed is:

1. A composition of matter comprising:
    a diamine wherein said diamine is selected from the group consisting of: straight, branched and cyclic aliphatic chains;
    a sulfoisophthalic acid;
    wherein the molar ratio of said diamine to said sulfoisophthalic acid is a 1:2 ratio or a 3:2 ratio.

2. The composition of matter of claim 1, wherein said diamine is selected from the group consisting of: a primary, a secondary, a tertiary, and combination of primary and secondary, and combination of primary and tertiary, a combination of secondary and tertiary, and a combination of primary, secondary and tertiary amines.

3. The composition of matter of claim 1, wherein said diamine is 1,6-hexamethylene diamine.

4. The composition of matter of claim 1, wherein said diamine is 1,4-butanediamine.

5. The composition of matter of claim 1, wherein said diamine is 2,2,4- and 2,4,4-trimethyl 1,6 hexanediamine.

6. The composition of matter of claim 1, wherein said diamine is 4,4'-methylenebis(cyclohexylamine).

7. The composition of matter of claim 1, wherein said diamine is N,N,N'N'-tetramethylethylenediamine.

8. The composition of matter of claim 1, wherein said composition comprises a mixed salt further comprising three diamine groups.

9. The composition of matter of claim 8, wherein each of said three diamine groups is different.

10. The composition of matter of claim 8, wherein two of said three diamine groups is different from a third of said three diamine groups.

11. The composition of matter of claim 8, wherein all of said three diamine groups are the same.

12. The composition of matter of claim 1, wherein said composition is provided in solution.

13. A method for producing a diamine salt of sulfoisophthalic acid, said method comprising:
    generating a sulfoisophthalic acid; and
    charging said sulfoisophthalic acid with diamine in a 1:2 ratio or a 3:2 ratio of said diamine to said sulfoisophthalic acid, wherein said sulfoisophthalic acid is a free acid.

14. The method of claim 13, wherein said diamine is selected from the group consisting of: straight, branched, and cyclic aliphatic chains.

15. The method of claim 13, wherein said diamine is selected from the group consisting of: a primary, a secondary, a tertiary, a combination of primary and secondary, a combination of primary and tertiary, a combination of secondary and tertiary, and a combination of primary, secondary and tertiary amines.

16. The method of claim 13, wherein said diamine is 1,6-hexamethylene diamine.

17. The method of claim 13, wherein said diamine is 1,4-butanediamine.

18. The method of claim 13, wherein said diamine is 2,2,4- and 2,4,4-trimethyl 1,6 hexanediamine.

19. The method of claim 13, wherein said diamine is 4,4'-methylenebis(cyclohexylamine).

20. The method of claim 13, wherein said diamine is N,N,N'N'-tetramethylethylenediamine.

21. The method of claim 13 wherein said step of generating comprises:
    adding isophthalic acid to oleum 30% to create a mixture at a first temperature range of about 60° C. to about 80° C.;
    heating said mixture to a temperature between about 190° to about 210° C.;
    holding said mixture at a temperature between about 190° C. to about 210° C.;
    cooling said mixture to a temperature about less than 170° C.;
    adding said mixture to a quantity of water to create an aqueous solution, while keeping the temperature below about 125° C.;
    cooling said mixture to a temperature between about 0° C. to about 125° C.;
    adding a solution of diamine while temperature is maintained between about 0° C. to about 125° C.;
    holding said mixture to a temperature between about 0° C. to about 125° C.;
    cooling said mixture to a temperature between about 0° C. to about 50° C.;
    holding said mixture at a temperature range of about 0° C. to about 50° C.;
    filtering said solution to isolate a solid;
    washing said solid; and
    drying said solid;
    wherein said solid is solid diaminium bis-3,5-dicarboxybenzensulfonate.

22. The method of claim 21, wherein the method further comprises:
    adding the solid diaminium bis-3,5-dicarboxybenzensulfonate to a solvent at a temperature between about 50° C. to about 125° C.;
    adding a solution of diamine while holding the temperature between about 50° C. to about 125° C.;
    holding said mixture at a temperature range of about 50° C. to about 125° C.;
    cooling said mixture to a temperature between about 0° C. to about 50° C.;
    holding said mixture at a temperature between about 0° C. to about 50° C.;
    filtering said mixture to isolate a solid;
    washing said solid; and
    drying said solid;
    wherein said solid is a tri-diaminium bis-3,5-dicarboxybenzensulfonate.

23. The method of claim 13, wherein said salt is diaminium bis-3,5-dicarboxybenzensulfonate.

* * * * *